United States Patent [19]

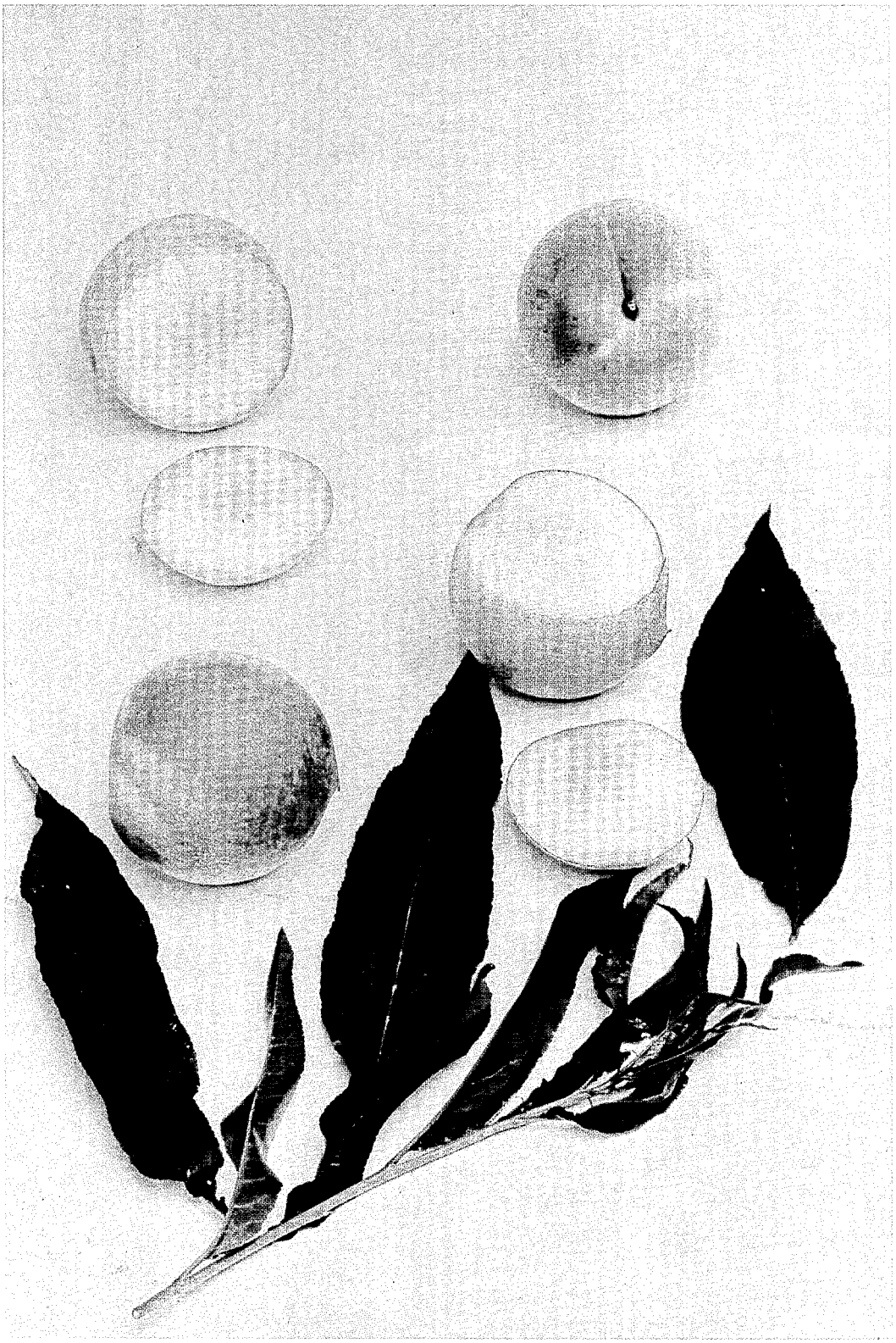

Minami

[11] Plant 4,064

[45] June 21, 1977

[54] PEACH TREE

[76] Inventor: William Y. Minami, P.O. Box 788, Reedley, Calif. 93654

[21] Appl. No.: 708,911

[22] Filed: July 26, 1976

[51] Int. Cl.[2] ..... A01H 5/03

[52] U.S. Cl. ..... Plt./43

[58] Field of Search ..... Plt./43

*Primary Examiner*—Robert E. Bagwill

*Attorney, Agent, or Firm*—Huebner & Worrel

[57] ABSTRACT

A peach tree generally similar to the Springcrest Peach Tree (unpatented) which bears early ripening, yellow fleshed, semi-freestone fruit from 7 to 10 days earlier than the Springcrest.

1 Drawing Figure

BACKGROUND OF THE VARIETY

The present invention relates to a new and distinct variety of peach tree broadly characterized by its regular and prolific bearing of early ripening, small to medium sized, firm and yellow fleshed, semi-freestone fruit and more particularly to such a peach tree further characterized by its similarity to the Springcrest (unpatented) variety except for its somewhat lighter foliage and, especially by the ripening of its fruit 7 to 10 days earlier.

The Springcrest peach tree, developed by the United States Department of Agriculture, is well known as producing highly attractive, early ripening, semi-freestone peaches of good quality and excellent market acceptance. As with all produce, the time of harvest of peaches greatly influences the prices the peaches bring on the market. Generally, the earlier an early ripening peach can be marketed the higher the price. This has been a contributing factor in the success of the Springcrest. The present variety virtually duplicates the high quality of the Springcrest but ripens from a week to 10 days earlier. It ripens approximately at the same time as the Springold (unpatented) but enjoys several advantages over it including less demanding chilling requirements for fruit production.

ORIGIN AND ASEXUAL REPRODUCTION OF THE NEW VARIETY

My new variety of peach tree was discovered by me in 1973 as a sport growing in an orchard of Springcrest peach trees on my farm at 20022 East Manning Ave., Reedley, Fresno County, Calif. Buds from the sport were budded by me at my above designated farm into Nemaguard (unpatented) peach tree rootstocks and the fruit and tree characteristics resulting from such budding proved identical to those of the original sport.

SUMMARY OF THE NEW VARIETY

The instant variety of peach tree is characterized by perpetuating the general characteristics of the Springcrest peach, but has the important distinction of ripening from 7 to 10 days earlier under the growing conditions prevailing in the San Joaquin Valley of California. The new peach tree is of vigorous growth. The fruit is of relatively uniform small to medium size and of globose form having a brilliant greenish yellow (7.5 Y 9/8) background which is mottled and streaked with dark red (5 R 3/7). The fruit is semi-freestone and has yellow, firm textured flesh.

BRIEF DESCRIPTION OF THE DRAWING

The accompanying drawing is a color photograph of four mature fruit of the subject variety with two of the fruit sliced to show flesh color together with a representative twig showing characteristic leaves.

DETAILED DESCRIPTION

Referring more specifically to the pomological details of this new and distinct variety of peach tree, the following has been observed under the ecological conditions prevailing at the orchard at Reedley, Fresno County, Calif., and is an outlined description thereof. All major color code plate identifications are by reference to the Nickerson Color Fan of the American Horticultural Council.

TREE

Size: Large, vigorous, with shape and density determined by pruning methods.

Leaves: Medium large.

- *Length.*—Average 150 mm.
- *Width.*—Average 43 mm.
- *Form.*—Lanceolate with apex acuminate.
- *Color.*—Upper surface, moderate olive green (5 Y 4/3); under surface, moderate olive green (2.5 Y 4/3).
- *Margin.*—Finely serrated.
- *Petiole.*—Average length 11 mm; average diameter 2 mm.
- *Gland.*—Varying in number from one to four on petioles and base of leaf, globose.
- *Stipules.*—None.

Flowers: Substantially the same as Springcrest (unpatented) and blooms at substantially the same time.

FRUIT

Maturity: 7 to 10 days before Springcrest, approximately May 20 at Reedley, Fresno County, Calif.

Size: Relatively uniform and dependent upon thinning practices, pruning and cultural practices.

- *Axial diameter.*—Average 55 mm. Transverse in suture plane — 56 mm. Transverse at right angles to suture plane — 57 mm.

Form: Generally globose, symmetrical.

- *Suture.*—Slight with yellow line, from base to apex with slight depression beyond pistil point.
- *Ventral surface.*—Rounded, lips unequal.

*Cavity.*—Rounded, average breadth 9 mm, average depth 9 mm.
*Pistil point.*—Definite.
*Stem.*—Average diameter 3 mm.

Skin:
*Thickness.*—Medium.
*Tendency to crack.*—None.
*Color.*—Ground color is brilliant greenish yellow (7.5 Y 9/8) mottled and streaked to solid, especially at apex, with dark red (5 R 3/7).
*Pubescence.*—Less than Springold (unpatented).

Flesh:
*Color.*—Generally brilliant yellow (2.5 Y 9/9) to strong yellow (2.5 Y 7/10) at apex.
*Juice.*—Juicy when ripe.
*Flavor.*—Excellent.
*Aroma.*—Aromatic, but not strongly so.
*Texture.*—Firm.
*Ripening.*—Evenly.
*Eating quality.*—Good.

Stone:
*Type.*—Semi-freestone.
*Size.*—Length, average 30 mm; breadth average 20 mm.
*Form.*—Oval, approaching globose.
*Sides.*—Rounded, often equal.
*Ventral Edge.*—Wing at base.
*Dorsal edge.*—Groove from base to center.
*Color.*—Pale orange yellow (7.5 YR 9/4).
*Splitting tendency.*—Minor.

Use: Fresh table.
*Keeping quality.*—Comparatively good.
*Shipping quality.*—Excellent in comparison with other varieties ripening at same time.

Although the new variety of peach tree possesses the described characteristics as a result of the growing conditions in Fresno County, Calif., in the central portion of the San Joaquin Valley, it is to be understood that variations of the usual magnitude in characteristics incident to growing conditions, fertilization, pruning, and pest control are to be expected.

Having thus described and illustrated my new variety of peach tree, what is claimed as new and desired to be secured by Letters Patent is:

1. A new and distinct variety of peach tree substantially as illustrated and described and which is characterized by its regular and prolific bearing of early ripening small to medium, semi-freestone, yellow-fleshed fruit; and by its general resemblance to the Springcrest (unpatented) peach tree, but from which it is distinguished by its fruit ripening from 7 to 10 days earlier.

* * * * *

UNITED STATES PATENT AND TRADEMARK OFFICE

CERTIFICATE OF CORRECTION

PATENT NO. : PP 4064

DATED : June 21, 1977

INVENTOR(S) : William Y. Minami

It is certified that error appears in the above-identified patent and that said Letters Patent are hereby corrected as shown below:

Column 2, Lines 27 and 28, delete "(5Y 4/3)" and substitute --- (5GY 4/3) ---.

Lines 28 and 29, delete "(2.5Y 4/3)" and substitute --- (2.5GY 4/3) ---.

Signed and Sealed this

*Sixth* Day of *September 1977*

[SEAL]

*Attest:*

RUTH C. MASON
*Attesting Officer*

LUTRELLE F. PARKER
*Acting Commissioner of Patents and Trademarks*